United States Patent
Ducharme et al.

(10) Patent No.: US 6,409,745 B1
(45) Date of Patent: Jun. 25, 2002

(54) FIELD-DEPLOYABLE FORCED AIR WARMING SYSTEM

(75) Inventors: Michel B. Ducharme, Kettleby; John Frim, Bramalea, both of (CA)

(73) Assignee: Her Majesty the Queen in right of Canada, as represented by the Minister of National Defence of Her Majesty's Canadian Government, Ottawa (CA)

(*) Notice: Subject to any disclaimer, the term of this patent is extended or adjusted under 35 U.S.C. 154(b) by 49 days.

(21) Appl. No.: 09/735,803

(22) Filed: Dec. 14, 2000

(51) Int. Cl.[7] .................................................. A61F 7/00
(52) U.S. Cl. ...................................... 607/108; 607/104
(58) Field of Search ................................ 607/108, 104, 607/107, 96; 5/627, 629; 219/211; 604/93.01, 113; 600/21; 135/128

(56) References Cited

U.S. PATENT DOCUMENTS

| | | | | |
|---|---|---|---|---|
| 4,389,066 A | * | 6/1983 | Weir et al. | |
| 5,350,417 A | * | 9/1994 | Augustine | 607/104 |
| 5,626,151 A | * | 5/1997 | Linden | 128/897 |
| 6,001,057 A | * | 12/1999 | Bongiovanni et al. | 600/21 |
| 6,321,764 B1 | * | 11/2001 | Gauger et al. | 135/128 |

* cited by examiner

*Primary Examiner*—Chen-Wen Jiang
(74) *Attorney, Agent, or Firm*—George A. Seaby (57) ABSTRACT

A portable, forced air apparatus for warming a hypothermia victim in the field includes a stretcher, strips of material extending across the stretcher for supporting the torso of the victim above the stretcher bottom, a canopy for covering the victim's torso, a blower operated heater in a compartment in the stretcher beneath the victim's legs for delivering hot air to the canopy in the area of the torso for warming the victim's body while the legs and arms are covered to prevent heat loss, a heated head and neck support for controlled warming of the victim's head and neck, and sleeves for covering the victim's arms and legs to prevent heat loss therefrom during torso warming. The heating system is complemented by warm IV infusion and warm oxygen delivery to the victim.

13 Claims, 8 Drawing Sheets

FIELD-DEPLOYABLE FORCED AIR WARMING SYSTEM

BACKGROUND OF THE INVENTION

1. Field of the Invention

This invention relates to a portable forced air warming apparatus for warming victims of hypothermia.

Severe hypothermia is a surprisingly common occurrence in cold areas of the world. Hypothermia is considered to be severe when there is a significant risk of spontaneous ventricular fibrillation, which can result in death of the victim. The risk of ventricular fibrillation increases significantly when the victim's core or deep body temperature is below 28° C. At such low core temperatures, the victim should be handled carefully because of his/her unstable condition. A severe hypothermia victim who has been cooled rapidly, e.g. during immersion in water, is preferably rewarmed rapidly. A severe hypothermia victim who has been cooled slowly, e.g. by exposure to cold air, is preferably rewarmed slowly. In any event, it is imperative to stop heat loss and to initiate rewarming of victims of hypothermia as soon as possible to optimize the chances of survival. During rescue operations in remote areas, it may take several hours to transport casualties from the rescue site to a hospital for treatment.

2. Discussion of the Prior Art

Warming apparatuses, some of which are portable, are disclosed by U.S. Pat. No. 5,300,101, which issued to S. D. Augustine et al on Apr. 5, 1994; U.S. Pat. No. 5,304,213, which issued to L. D. Berke et al on Apr. 19, 1994; U.S. Pat. No. 5,336,249, which issued to I. Mahawili on Aug. 9, 1994; U.S. Pat. No. 5,350,417, which issued to S. D. Augustine on Sep. 27, 1994 and U.S. Pat. No. 6,001,057, which issued to R. A. Bongiovanni et al on Dec. 14, 1999.

The inventors have determined that when rewarming a hypothermia victim, it is preferable to heat the torso only while preventing heat loss from the extremities. Heating of the victim's limbs causes the return of cold blood to the torso which contributes to a core temperature drop that can decrease the chances of survival.

Very few warming apparatuses are available in the marketplace, and those that do exist consist of heated blankets or bags for heating a victim's entire body and extremities, and devices for providing warm air for inhalation by the victim. A need exists for a system for eliminating heat loss and initiating rewarming of a hypothermia victim in the field.

GENERAL DESCRIPTION OF THE INVENTION

An object of the present invention is to meet the above need by providing a relatively simple, portable, forced air warming apparatus, which is easily transported to the field, and which can be used for controlled heating of a victim's body.

Another object of the invention is to provide a portable warming apparatus which can be used to warm a victim's body only while preventing heat loss from the extremities.

Yet another object of the invention is to provide a warming apparatus which can be used to effect controlled warming of the victim's head and neck which contributes to warming of the central nervous system, and helps a victim to regain normal respiratory and cardiovascular functions.

In its simplest form, the invention relates to a portable warming apparatus for warming a hypothermia victim comprising a stretcher, said stretcher including a bottom wall, side walls and end walls contiguous with each other; a support extending between said side walls for supporting the body of a hypothermia victim, openings in said support permitting the circulation of warm air around the torso of the victim, a canopy for covering the torso of the victim and defining a heating chamber around the torso with said stretcher; at least one heating duct in said chamber for discharging warm air against the torso of the victim, whereby the warm air circulates through said openings around the torso; and a forced air heater for warming ambient air, and delivering the warm air to the heating duct.

BRIEF DESCRIPTION OF THE DRAWINGS

The invention is described below in greater detail with reference to the accompanying drawings, which illustrate a preferred embodiment of the invention, and wherein.

DESCRIPTION OF THE PREFERRED EMBODIMENT

Figure 1:
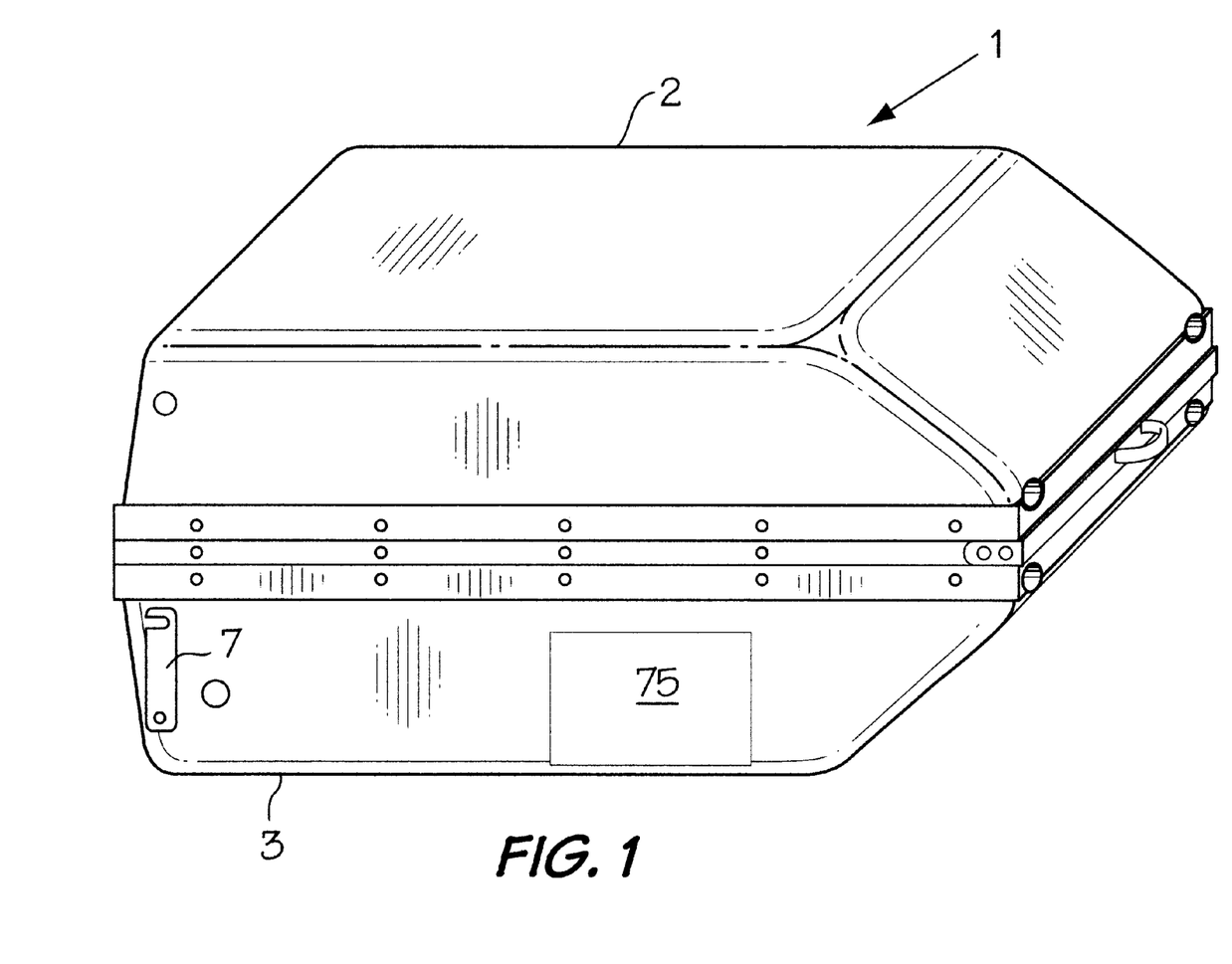
FIG. 1 is a perspective view of a portable warming apparatus in accordance with the present invention in the closed condition.
Figure 2:
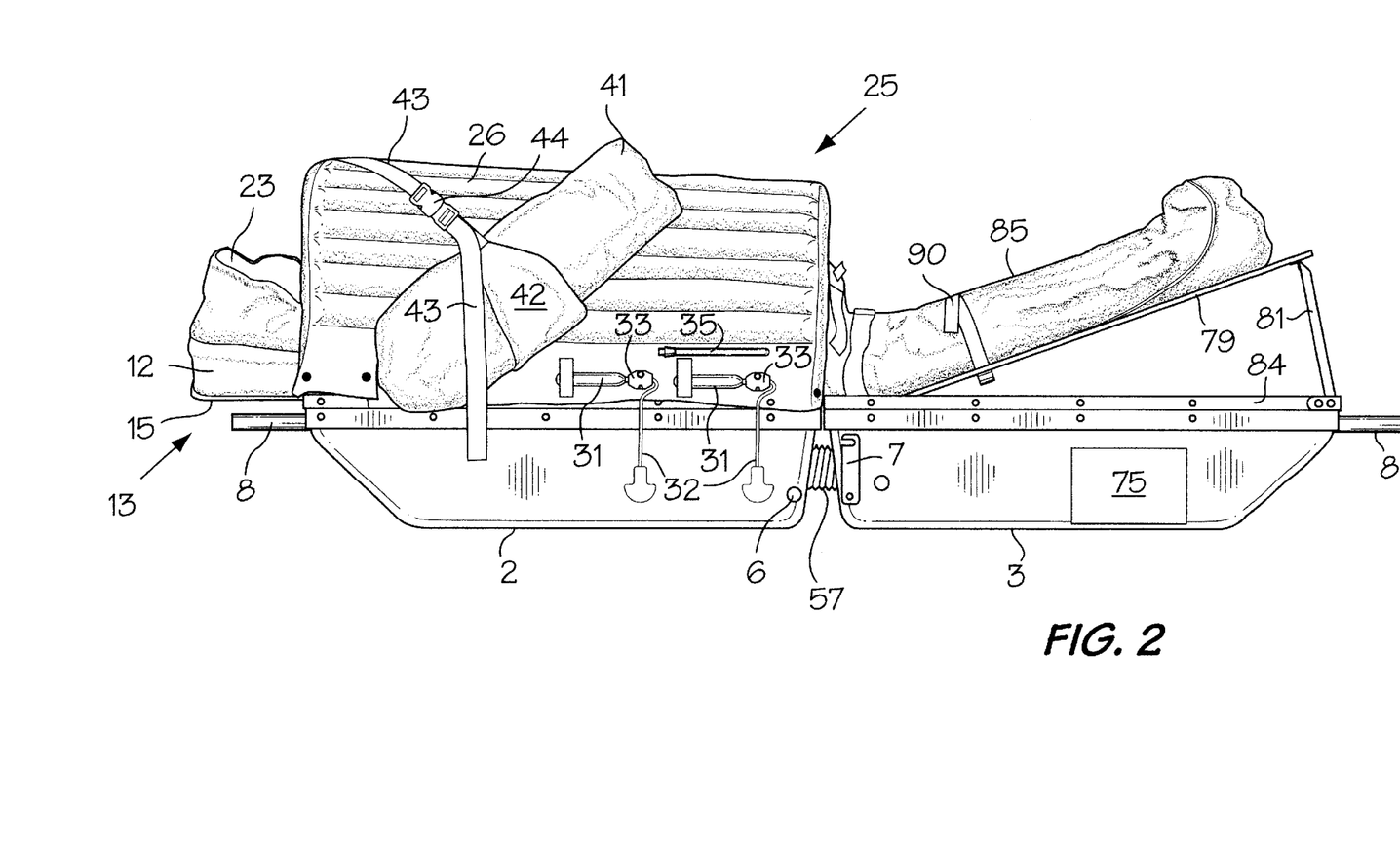
FIG. 2 is a side view of the warming apparatus of FIG. 1 in the open, use condition.
Figure 3:
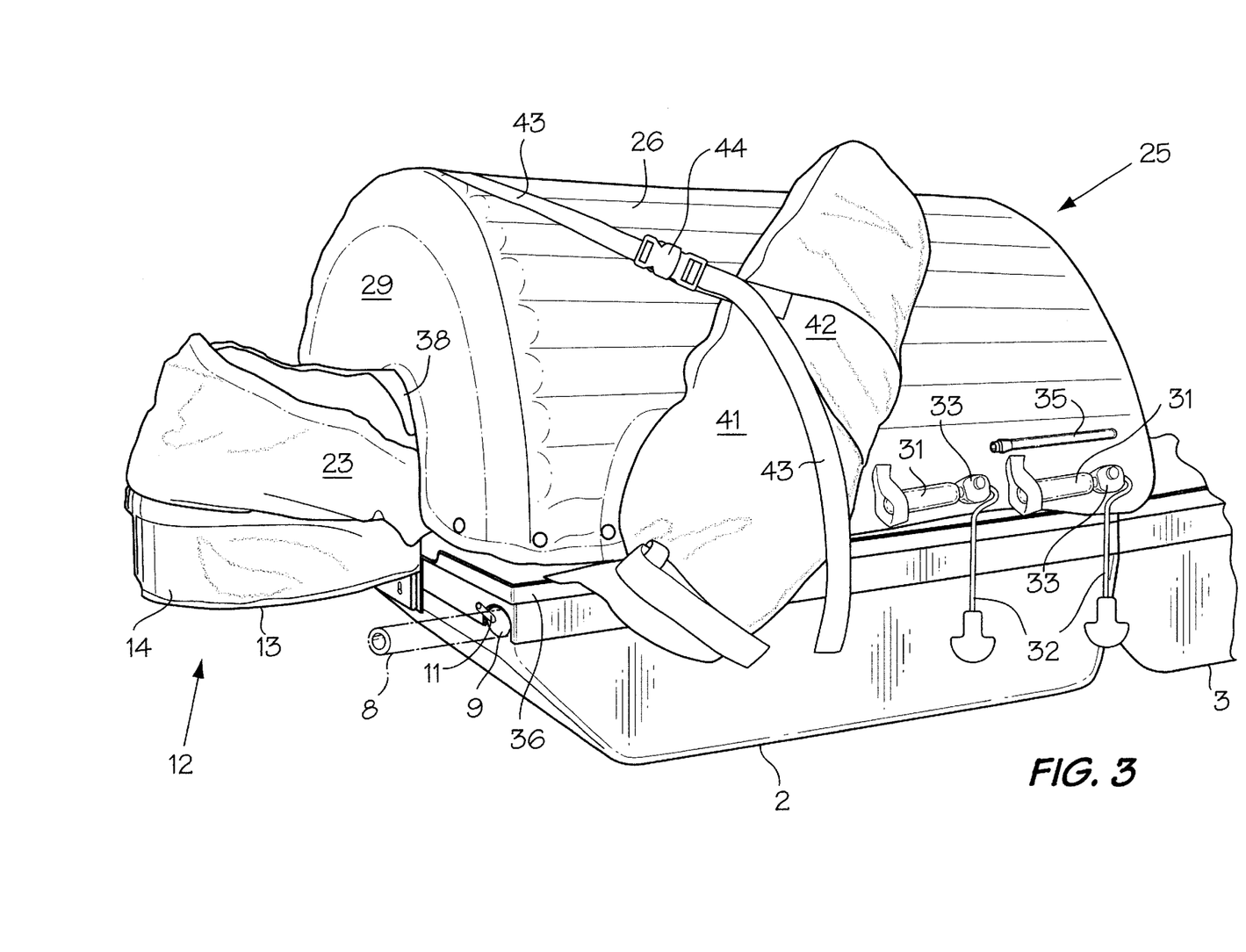
FIG. 3 is a perspective view of one end of the apparatus of FIGS. 1 and 2 in the use condition.
Figure 8:
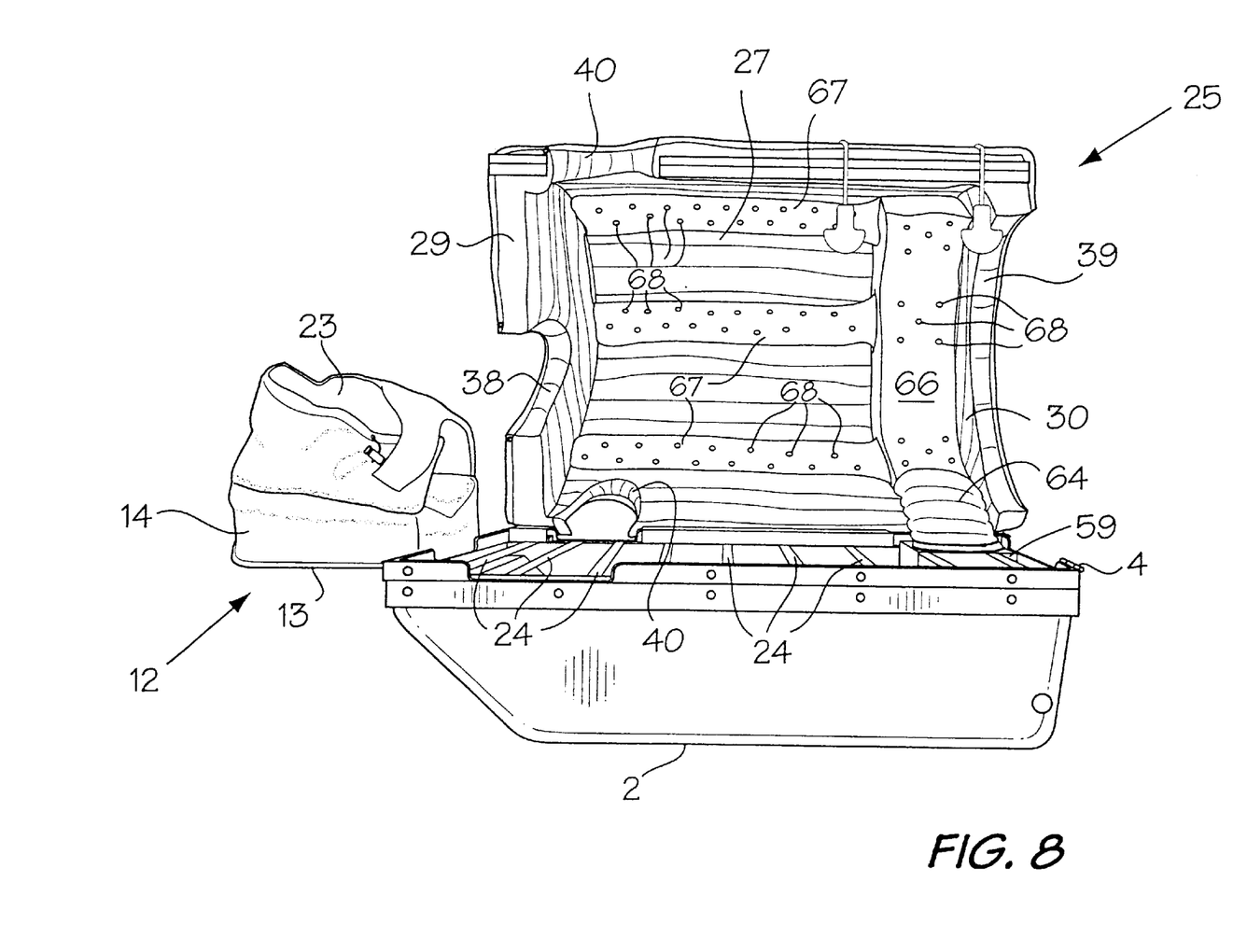
FIG. 8 is a perspective view of a second shell and canopy used in the apparatus of FIGS. 1 to 3 in the open, use condition.
Figure 9:
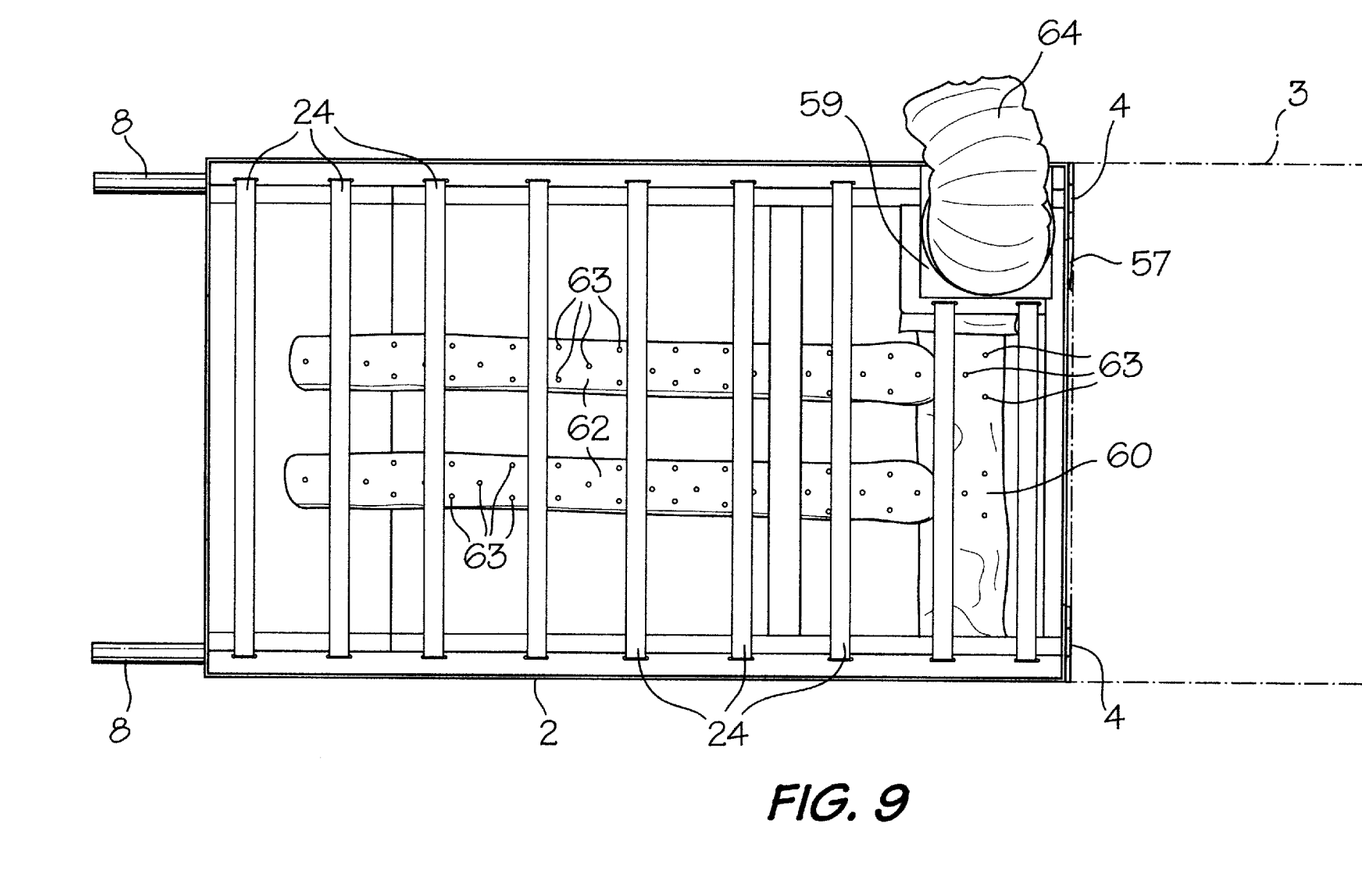
FIG. 9 is a top view of the shell of FIG. 8.
Figure 10:
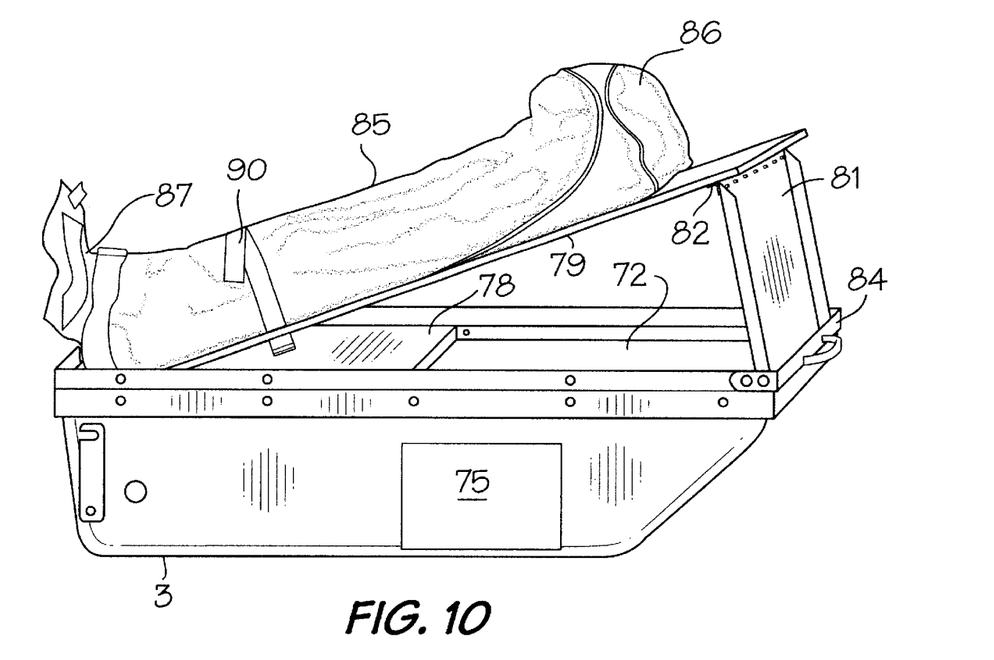
FIG. 10 is a perspective view of the shell of FIG. 7.

Referring to FIGS. 1 to 3, the warming system of the present invention includes a housing generally indicated 1 defined by two rectangular shells 2 and 3, which are connected together by hinges 4 (FIGS. 8 and 9) to define a generally rectangular box, which can be easily carried into the field on a vehicle such as a snowmobile, an all terrain vehicle or a trailer. The housing 1 is releasably locked in the open position by a latch mechanism defined by a pin 6 on one shell 2, and a notched arm 7, which is pivotally mounted on the other shell 3 of the housing. In the fully open position (FIG. 2), the housing shells 2 and 3 define an elongated stretcher for receiving and transporting a patient. To facilitate manual lifting and carrying of the housing in the open or use condition, tubular handles 8 are provided in the housing. The handles 8 (FIGS. 2 and 3) are slidably mounted in sockets 9 in the corners of the outer free ends of the shells 2 and 3 for movement between retracted positions (not shown) in the housing 1, and extended, use positions. The handles 8 are retained in the retracted, non-use positions by small latches 11, which are pivotally mounted on the ends of the shells 2 and 3 for rotation into and out of the path of travel of the handles 8.

Figure 4:
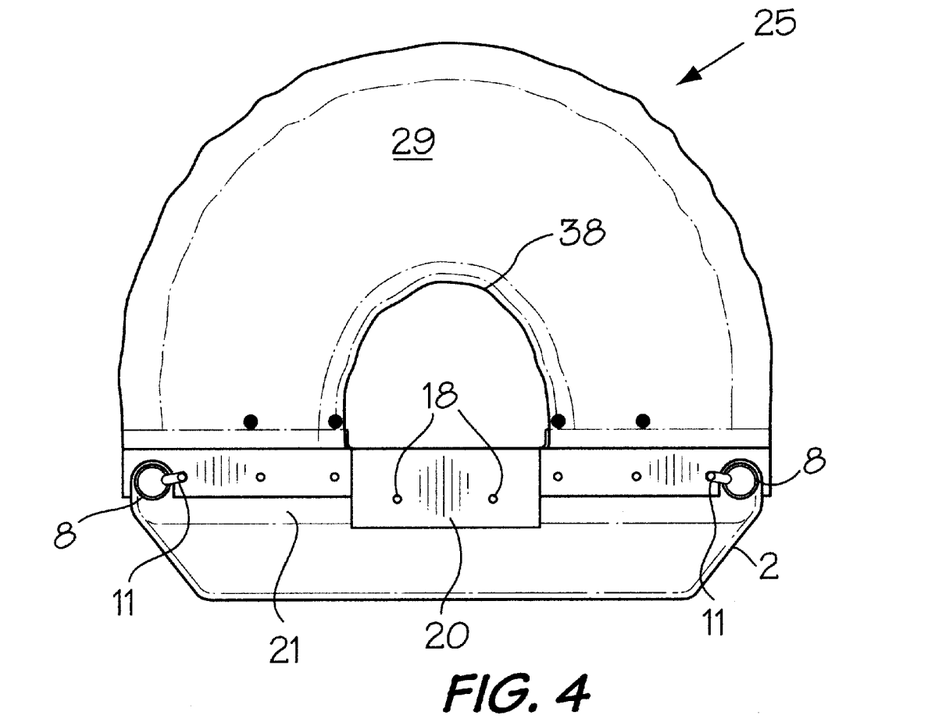
FIG. 4 is an end view of a housing used in the apparatus of FIGS. 1 and 2.
Figure 5:
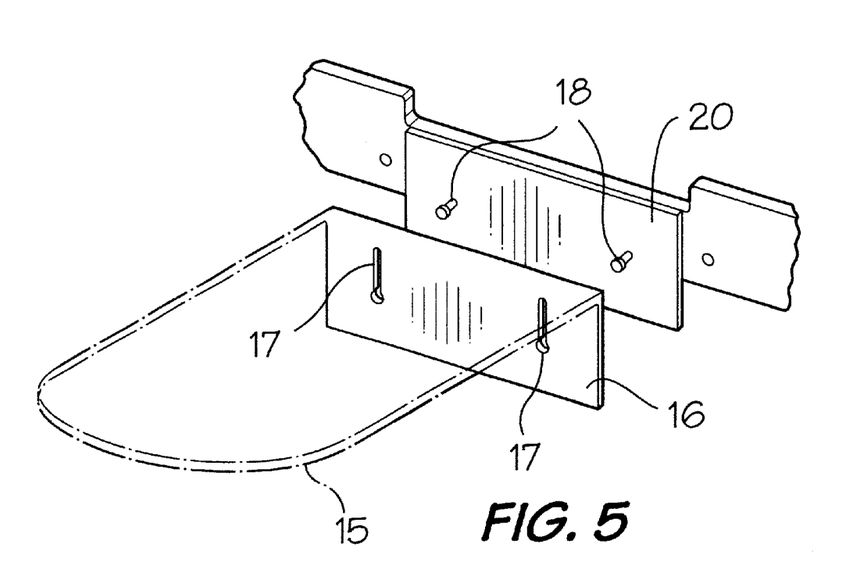
FIG. 5 is a perspective view of a head and neck support platform use in the apparatus of FIGS. 1 to 3.

The patient's head and neck are supported by a headrest generally indicated at 12. The headrest 12 is defined by a platform 13 carrying a cushion 14. The platform 13 is a thin, metal, generally L-shaped panel. A short arm 16 at one end of the platform 13 includes keyhole slots 17 for releasably mounting the platform 13 on pins 18 extending outwardly from a plate 20 (FIGS. 4 and 5) on one end 21 of the shell 2. The sides of the patient's head are covered by a hood 23, which is integral with the cushion 14.

The shell 2 contains a plurality of spaced apart strips 24 (in this case nylon) for supporting the torso of a patient. The strips 24 extend transversely of the housing between the sides of the shell 2. The spaced apart strips 24 promote air flow around the patient's torso. However, other supports with openings permitting air circulation around the patient can be used. For example, the strips 24 can be replaced by a perforated sheet or panel.

An inflatable, semicylindrical canopy generally indicated at 25 is mounted on the open top of the shell 2. The canopy 25 is defined by outer and inner shells 26 and 27, respectively, and arcuate end walls 29 and 30. The canopy 25 is stored in the shell 3 when the housing 1 is closed, i.e. not in use. After the housing 1 is opened, the canopy is removed and inflated using $CO_2$ cartridges 31 carried by the canopy. In order to inflate the canopy 25, an actuation cord 32 is pulled to open a valve 33 on one of the cartridges 31, admitting $CO_2$ to the canopy through the valve. Excess pressure in the canopy 25 is released using hose 35 containing a one-way exhaust valve. The canopy 25 is attached to flanges 36 on the periphery of the shell 2 to surround the top and sides of the torso of the patient. The head and neck of the patient extend through a generally semicircular notch 38 in one end wall 29, and the hips and legs of the patient extend through a similar notch 39 in the other end wall 30 (FIG. 8) of the canopy 25. Notches 40 in the bottom side edges of the canopy 25 receive the arms of the patient, so that the arms extend out of the canopy.

Figure 6:
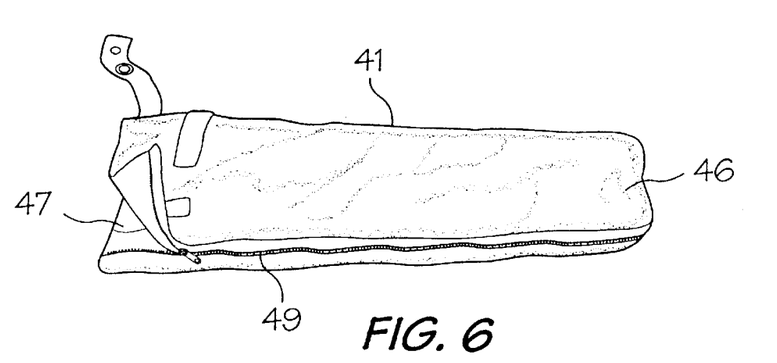
FIG. 6 is a perspective view of a sleeve used in the apparatus of FIGS. 1 to 3.

The arms of the patient are covered by insulated sleeves 41. Each sleeve 41 is attached to the canopy 25 by a flap 42 sewn to the sleeve 41, straps 43 and buckles 44. With the buckle 44 released, the sleeve 41 can be moved to accept a patient's arm. Once the arm is positioned in the sleeve 41, the buckle 44 is closed to secure the arm in position against the canopy 25. As best shown in FIG. 6, the sleeve 41 is tubular with a closed end 46 and an open end 47 for receiving a patient's arm. A zipper 49 extends longitudinally of the sleeve 41 permitting access to a patient's arm for connecting an IV line or for administering medicine.

Figure 7:
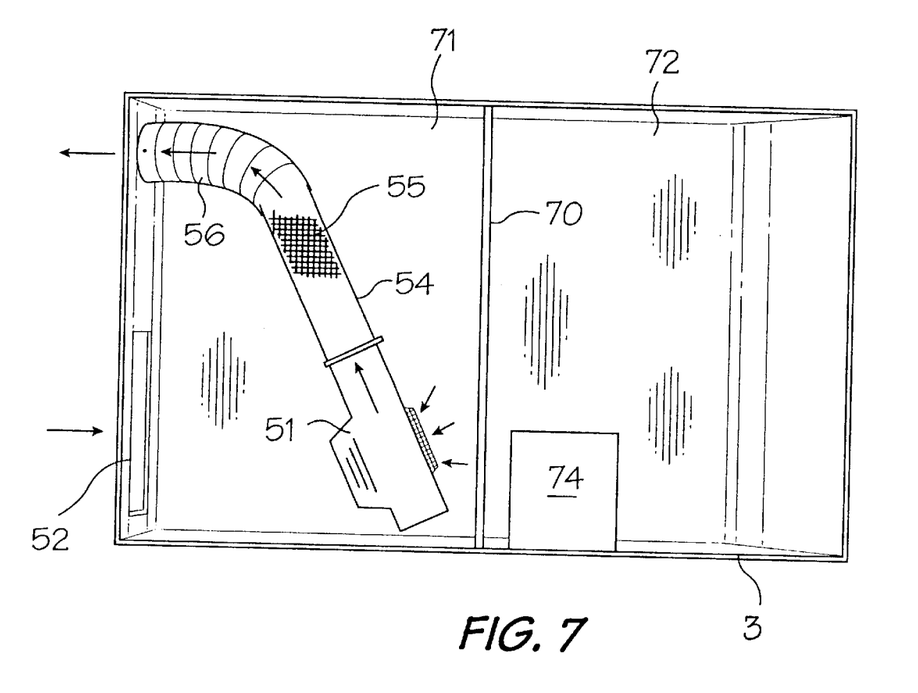
FIG. 7 is a schematic top view of a shell used in the apparatus of FIGS. 1 to 3.

With the canopy 25 closed, the torso of the patient is warmed using a hot air system. Referring to FIG. 7, the hot air heating system includes a blower 51 mounted in the shell 3. The blower 51 receives air via an opening 52 in one end of the shell 3. The air is circulated between the shells 2 and 3. Air exhausted from one end of the sheet 2 through an opening (not shown) flows through the opening 52 into the shell 3. The opening 52 and the opening the shell 2 are closed when the apparatus is not in use, i.e. during storage or transport. The air discharged from the blower 51 passes through a duct 54 containing a pair of heating elements and a heat exchanger (illustrated schematically at 55), and then through a flexible tube 56 and an opening (not shown) in the shell 3. The warm air passes through plastic connectors 57 at the ends of the shells 2 and 3. The holes in the shells 2 and 3 are plugged by canopies (not shown) fixed to the shells when the system is not in use. The warm air enters into one end of a box 59 in one end of the shell 2. A manifold 60 (FIG. 9), defined by a plastic tube with a closed outer free end (not shown) extends out of the box 59 across the end of the shell 2. A pair of plastic tubes or ducts 62 extend out of the manifold 60 longitudinally of the shell 2. The closed outer to ends of the ducts 60 are anchored to the end wall of the shell 2. Perforations 63 in the manifold 60 and the ducts 62 discharge warm air into the shell 2 beneath the strips 24.

A flexible tube 64 extending out of the top of the box 59 carries warm air to a manifold 66 (FIG. 8) extending transversely of one end of the canopy 25. Ducts 67 carry air from the manifold 66, the length of the canopy. The free ends of the manifold 66 and of the ducts 67 are closed. Perforations 68 in the manifold 66 and in the ducts 67 discharge warm air into the top of the chamber defined by the shell 2 and the canopy 25.

Referring again to FIG. 7, the interior of the shell 3 is divided by a partition 70 into a compartment 71 containing the blower 51, the duct 54, the heaters and heat exchangers 55 and the tube 56, and a storage compartment 72 containing a control box 74. The controls (not shown) for the blower 51, heater 55 and the heater in the cushion 12 are located on a control panel 75 (FIG. 2) which forms the outer wall of the control box 74 and is accessible from outside of the shell. The control box has preset controls for the speed of the blower 51 and the intensities of the heaters to provide different levels of heating power to the torso of a victim. The storage compartment 72 is used to store the canopy 25 and the head supporting elements during storage or transporting.

When the apparatus is not in use, the storage compartment 72 is closed by a panel 79, which is also used as a support for the legs of a patient during use of the apparatus. The cover/leg support panel 79 supports the legs of the patient in an inclined position. For such purpose, a leg 81 is connected to one end of the panel 79 by a piano hinge 82. The bottom end of the leg 81 is maintained in position by a flange 84 extending around the two sides and the free end of the shell 3.

Figure 11:
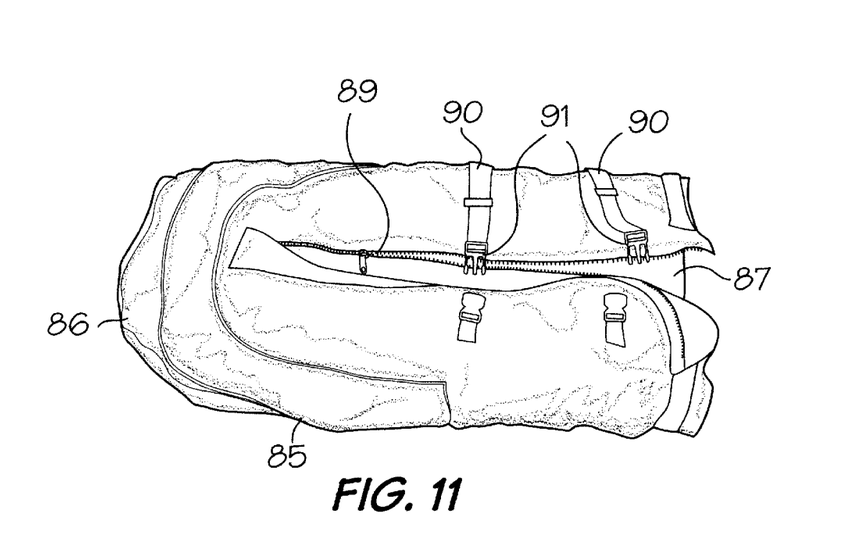
FIG. 11 is a perspective view of a leg bag used in the apparatus of FIGS. 1 to 3.

Referring to FIG. 11, an insulated bag 85 is used to cover the legs of a patient. The bag 85 is tubular with a closed bottom end 86 and an open top end 87 for receiving the patient's legs. A longitudinally extending zipper 89 facilitates insertion of the legs into the bag. A second zipper (not shown) extends across the closed end 86 of the bag 85 to facilitate access to the feet of a patient, without opening the zipper 89. The bag 76 is made snug around the legs of a patient by straps 90 and buckles 91. During storage or transporting of the apparatus, the bag 76 for the patient's legs remains on the panel 79.

Thus, in its simplest form the apparatus described above includes a stretcher for supporting a hypothermia victim while warm air is circulated around the torso of the victim. The invention can be incorporated in a modified, commercially available stokes litter. Such a device would be admirably suited to certain search and rescue operations, e.g. ground search and rescue.

It should also be noted that the apparatus described herein can be used for complete treatment of hypothermia victims in the field, including the administering of warm IV fluid to correct dehydration and improve circulation, and warm oxygen to assist in the oxygenation of tissues and decrease the risk of infection. An IV fluid bag and an $O_2$ tank are carried in the stretcher beneath a victim. The containers are warmed by activating the heating system before placing a patient on the stretcher.

We claim:

1. A portable apparatus for warming a hypothermia victim comprising a stretcher, said stretcher including a bottom wall, side walls and end walls contiguous with each other; a support extending between said side walls for supporting the torso of a hypothermia victim above and spaced apart from the bottom wall of the stretcher; openings in said support permitting the circulation of warm air around the torso of the victim, a canopy for covering the torso of the victim and defining a heating chamber around the torso with said stretcher; heating ducts in said chamber for discharging warm air against the torso of the victim, whereby the warm air circulates through said openings around the torso; and a forced air heater for warming ambient air, and delivering the warm air to the heating ducts.

2. The apparatus of claim 1, wherein said stretcher includes first and second shells; and hinges pivotally interconnecting said first and second shells for rotation between a compact closed position and an open use position, said support being located in said first shell.

3. The apparatus of claim 2, wherein each said first and second shell includes a bottom wall, side walls, end walls and an open top end.

4. The apparatus of claim 3, wherein said support includes a plurality of spaced apart strips extending across the open top end of said first shell for supporting the torso of a victim.

5. The apparatus of claim 2, wherein said forced air heater includes a blower in said second shell for receiving ambient air, a heater in fluid communication with said blower for warming ambient air, a first manifold in one end of said first shell for receiving warm air from said heater; a second manifold in said canopy for receiving warm air from said heater, said first and second manifolds being connected to said heating ducts for distributing warm air thereto.

6. The apparatus of claim 5, wherein said first manifold extends transversely of said one end of said first shell, said second manifold extends transversely of one end of said canopy, and said heating ducts extend longitudinally of said first shell and said canopy.

7. The apparatus of claim 2, including a panel in said second shell for supporting the legs of a victim, and a collapsible leg on said panel for supporting the panel and the legs of a victim in an inclined position.

8. The apparatus of claim 7, including a bag for covering the legs of a victim during warming of the torso to prevent heat loss to the legs.

9. The apparatus of claim 8, including sleeves for covering the arms of a victim during warming of the torso to prevent heat loss to the arms.

10. The apparatus of claim 1, wherein said canopy includes an inflatable, semicylindrical body having first and second closed ends, a first semicircular opening in said first end for receiving the neck of a victim, and a second semicircular opening in said second end for receiving the bottom of the body of a victim.

11. The apparatus of claim 10, wherein said canopy body is inflatable.

12. The apparatus of claim 1, including a heated headrest for supporting the head and neck of a victim.

13. The apparatus of claim 12, wherein said headrest includes a platform for removable connection to one end of said stretcher, a heated cushion for supporting the head of a victim of hypothermia, and a hood for covering the sides of the head of the victim.

\* \* \* \* \*